United States Patent
Bonrath et al.

(10) Patent No.: US 11,851,402 B2
(45) Date of Patent: Dec. 26, 2023

(54) SPECIFIC DEHYDROGENATION PROCESS (I)

(71) Applicant: DSM IP ASSETS B.V., Heerlen (NL)

(72) Inventors: Werner Bonrath, Kaiseraugst (CH); Marc-André Mueller, Kaiseraugst (CH); Bettina Wuestenberg, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 94 days.

(21) Appl. No.: 17/603,114

(22) PCT Filed: Apr. 3, 2020

(86) PCT No.: PCT/EP2020/059477
§ 371 (c)(1),
(2) Date: Oct. 12, 2021

(87) PCT Pub. No.: WO2020/212163
PCT Pub. Date: Oct. 22, 2020

(65) Prior Publication Data
US 2022/0194891 A1    Jun. 23, 2022

(30) Foreign Application Priority Data
Apr. 15, 2019  (EP) ..................... 19169206

(51) Int. Cl.
| | | |
|---|---|---|
| *C07C 5/327* | (2006.01) | |
| *C07C 67/44* | (2006.01) | |
| *C07C 67/02* | (2006.01) | |
| *C07C 69/145* | (2006.01) | |
| *C07C 69/24* | (2006.01) | |
| *C07C 5/44* | (2006.01) | |
| *C07C 403/14* | (2006.01) | |

(52) U.S. Cl.
CPC ............. *C07C 5/327* (2013.01); *C07C 5/44* (2013.01); *C07C 67/02* (2013.01); *C07C 67/44* (2013.01); *C07C 69/145* (2013.01); *C07C 69/24* (2013.01); *C07C 403/14* (2013.01); *C07C 2601/16* (2017.05)

(58) Field of Classification Search
CPC ....... C07C 69/24; C07C 69/145; C07C 67/02; C07C 67/44; C07C 2601/16; C07C 5/42; C07C 5/44; C07C 5/327
See application file for complete search history.

(56) References Cited

U.S. PATENT DOCUMENTS 4,825,006 A    4/1989 Junzo et al.

FOREIGN PATENT DOCUMENTS

DE    1254613    * 11/1967    ........... C07C 403/14

OTHER PUBLICATIONS

Tutorskaya et al., Synthetic investigations in the chemistry of polyene compounds. LII. Synthesis of retinoic and dihydroretinoic esters by te Reformatski reaction, Journal of Organic Chemistry of the USSR, vol. 27, No. 7, pp. 1237-1240 (Year: 1991).*
Law et al., THe necessity of intact polyene for the biological isomerisation of vitamin A, Journal of the American Chemical Society, vol. 110, No. 17, pp. 5915-5917 (Year: 1988).*
DE 1244613, Koenig, et al., Process for preparing vitamin A aldehyde, English translation 4 pages (Year: 1967).*
International Search Report and Written Opinion of the ISA for PCT/EP2020/059477 dated Jun. 22, 2020, 14 pages.
Duhamel et al., "The OSM (oxidation state modification) concept: application to a new and rapid synthesis of retinoids", Tetrahedron Letters, vol. 35, No. 8, Feb. 21, 1994, 2 pages.
Tutorskaya et al., "Synthetic investigations in the chemistry of polyene compounds. LII. Synthesis of retinoic and dihydroretinoic esters by the Reformatskii reaction", Journal of Organic Chemistry of the USSR, vol. 27, No. 7, Jul. 1991, pp. 1237-1240.
Law et al., "The necessity of an intact polyene for the biological isomerisation of vitamin A", Journal of the American Chemical Society, vol. 110, No. 17, Aug. 1988, pp. 5915-5917.

* cited by examiner

*Primary Examiner* — Yate' K Cutliff
(74) *Attorney, Agent, or Firm* — NIXON & VANDERHYE P.C.

(57) ABSTRACT

The present invention relates to a new dehydrogenation process of specific compounds.

12 Claims, No Drawings

SPECIFIC DEHYDROGENATION PROCESS (I)

This application is the U.S. national phase of International Application No. PCT/EP2020/059477 filed Apr. 3, 2020 which designated the U.S. and claims priority to EP Patent Application No. 19169206.0 filed Apr. 15, 2019, the entire contents of each of which are hereby incorporated by reference.

Specific Dehydrogenation Process (I)

The present invention relates to a new dehydrogenation process.

The new dehydrogenation process according to the invention is a dehydrogenation of the following compounds of formula (I):

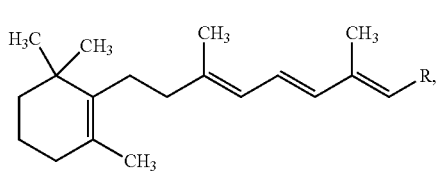

wherein
R is —CH=O or —CH$_2$OCOR', wherein R' is a C$_1$-C$_{16}$ alkyl group.

The dehydrogenation is taking place at the 7,8 position. The obtained products are compounds of formula (II):

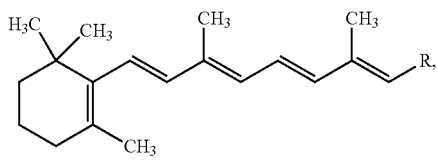

wherein
R is —CH=O or —CH$_2$OCOR', wherein R' is a —C$_1$-C$_{16}$ alkyl group (preferably —CH$_3$ or —(CH$_2$)$_{14}$CH$_3$).

The two dehydrogenation products are those of formula (IIa) and (IIb)

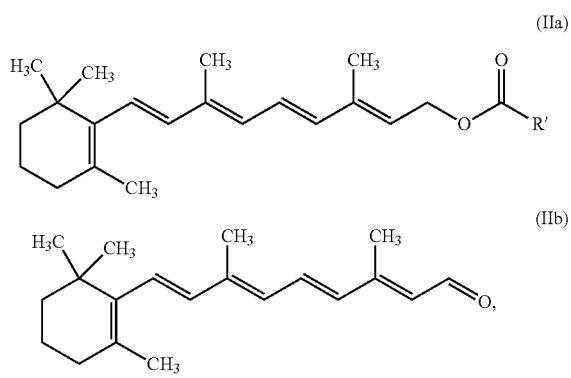

wherein R' has the same meaning as defined above.
The compound of formula (I) as well as of formula (II) can have any possible stereoisomeric form. Due to the 3 or 4 C—C-double bonds, there is variety of stereoisomeric forms. For the present invention the stereochemistry of the compounds of formula (I) and (II) is not essential.

The compound of formula (IIb) is an important intermediate in organic synthesis (especially in the synthesis of vitamin A and/or its derivatives).

From O. O. Tutorskaya et al (Zh.Org.i Khim. 1991, 27,1414) similar dehydrogenations are known, but the yield obtained therein are low (31%) and the obtained compound, the carboxylic ester, is more difficult to be converted into the vitamin A acetate.

Due to the importance of vitamin A acetate and its intermediates, there is always a need to provide new processes to produce such compounds.

Surprisingly, it was found that the compounds of formula (II) can be produced by the specific dehydrogenation of the compounds of formula (I).

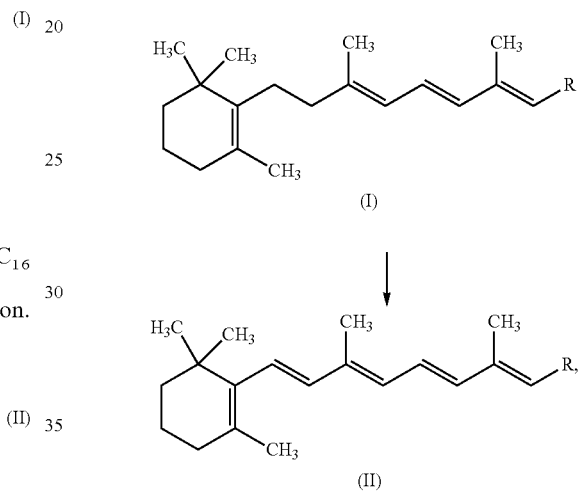

wherein R has the same meaning as defined above.
This process is easy to handle, and it allows to provide a possibility to shorten the synthesis of vitamin A (and its derivatives).

The process of the present invention is carried out in the presence of at least one specific oxidative reactant.

The oxidative reactant used in the process of the present invention has the following formula (III)

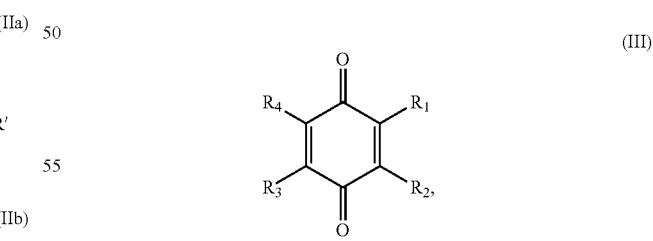

wherein
R$_1$ is —CN, —Cl or —F,
R$_2$ is —CN, —Cl or —F,
R$_3$ is —H, —CH$_3$, —Cl or —F, and
R$_4$ is —H, —CH$_3$, —Cl or —F.

Therefore, the present invention relates to a process (P) for the production of the compounds of formula (II):

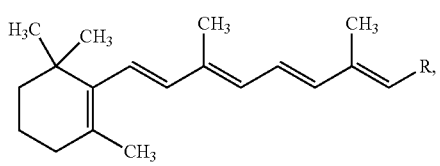

(II)

wherein
R is —CH=O or —CH$_2$OCOR', wherein R' is a —C$_1$-C$_{16}$ alkyl group (preferably —CH$_3$ or —CH$_2$CH$_3$),
by selective dehydrogenation of the compounds of formula (I):

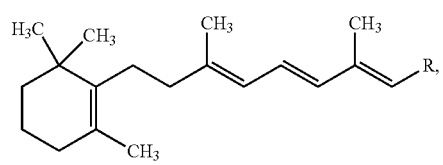

(I)

wherein
R has the same meanings as in the compound of formula (II), wherein the dehydrogenation is carried out in the presence of at least one oxidative reactant of formula (III):

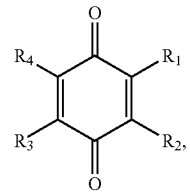

(III)

wherein
R$_1$ is —CN, —Cl or —F,
R$_2$ is —CN, —Cl or F,
R$_3$ is —H, —CH$_3$, —Cl or —F, and
R$_4$ is —H, —CH$_3$, —Cl or —F.

Preferred oxidative reactants of formula (III) are those of the following formula (IIIa), (IIIb) and (IIIc):

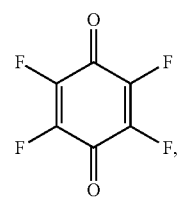

(IIIa)

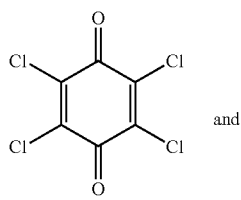

(IIIb)

and

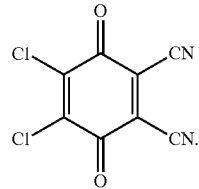

(IIIc)

Very preferred is the compound of formula (IIIc).

Therefore, the present invention relates to a process (P1) for the production of the compounds of formula (II), which is process (P), wherein the oxidative reactant is chosen from the group consisting of the compounds of formula (IIIa), (IIIb) and (IIIc)

(IIIa)

(IIIb)

and (IIIc)

Therefore, the present invention relates to a process (P2) for the production of the compounds of formula (II), which is process (P), wherein the oxidative reactant is the compound of formula (IIIc).

The amount of the oxidative reactant of formula (III) used in the process according to the present invention can vary. The amount of the oxidative reactant of formula (III) usually goes from 0.5 mol-equivalent up to 5 mol-equivalent (in relation to compound of formula (II)). Preferably from 1 to 3 mol-equivalent (in relation to compound of formula (II)).

Therefore, the present invention relates to a process (P2') for the production of the compounds of formula (II), which is process (P2), wherein the amount of the oxidative reactant of formula (III) goes from 0.5 mol-equivalent up to 5 mol-equivalent (in relation to compound of formula (II)).

Therefore, the present invention relates to a process (P2") for the production of the compounds of formula (II), which is process (P2), wherein the amount of the oxidative reactant of formula (III) goes from 1 to 3 mol-equivalent (in relation to compound of formula (II)).

The process according to the present invention can also be carried out in the presence of at least one additive compound. This additive compound is usually chosen from the group consisting of pyridine, butylhydroxyltoluol, hydroquinone and triethoxyamine.

The additive compound(s) is (are) added in amount of 0.001-1 mol-equivalent (in relation to compound of formula (II)), preferably 0.003-1 mol-equivalent (in relation to compound of formula (II)).

Therefore, the present invention relates to a process (P3) for the production of the compounds of formula (II), which is process (P), (P1), (P2), (P2') or (P2"), wherein the process is carried out in the presence of at least one additive compound.

Therefore, the present invention relates to a process (P3') for the production of the compounds of formula (II), which is process (P3), wherein the additive compound is chosen from the group consisting of pyridine, butylhydroxyltoluol, hydroquinone and triethoxyamine.

Therefore, the present invention relates to a process (P3") for the production of the compounds of formula (II), which is process (P3) or (P3'), wherein the additive compound is added in amount of 0.001-1 mol-equivalent (in relation to compound of formula (II)).

Therefore, the present invention relates to a process (P3''') for the production of the compounds of formula (II), which is process (P3) or (P3'), wherein the additive compound is added in amount of 0.003-1 mol-equivalent (in relation to compound of formula (II)).

The reaction is usually carried out in an inert solvent. The solvent is usually an aromatic hydrocarbon such as benzene or toluol.

Therefore, the present invention relates to a process (P4) for the production of the compounds of formula (II), which is process (P), (P1), (P2), (P2'), (P2"), (P3), (P3'), (P3") or (P3'''), wherein the process is carried out in the presence of at least one inert solvent.

Therefore, the present invention relates to a process (P4') for the production of the compounds of formula (II), which is process (P4), wherein the solvent is an aromatic solvent.

Therefore, the present invention relates to a process (P4") for the production of the compounds of formula (II), which is process (P4), wherein the solvent is chosen from the group consisting of benzene and toluol.

The process according to the present is usually carried out at elevated temperatures. Usually the process according to the present invention is carried out at a temperature of from 0° C.-120° C., preferably from 5° C.-100° C.

Therefore, the present invention relates to a process (P5) for the production of the compounds of formula (II), which is process (P), (P1), (P2), (P2'), (P2"), (P3), (P3'), (P3"), (P3'''), (P4), (P4') or (P4"), wherein the process is carried out at a temperature of from 0° C.-120° C.

Therefore, the present invention relates to a process (P5') for the production of the compounds of formula (II), which is process (P), (P1), (P2), (P2'), (P2"), (P3), (P3'), (P3"), (P3'''), (P4), (P4') or (P4"), wherein the process is carried out at a temperature of from 5° C.-100° C.

Furthermore, some of the starting material for the process according to the present invention are new.

The following three compounds (compounds for formulae (Ia), (Ib) and (Ic)) are new

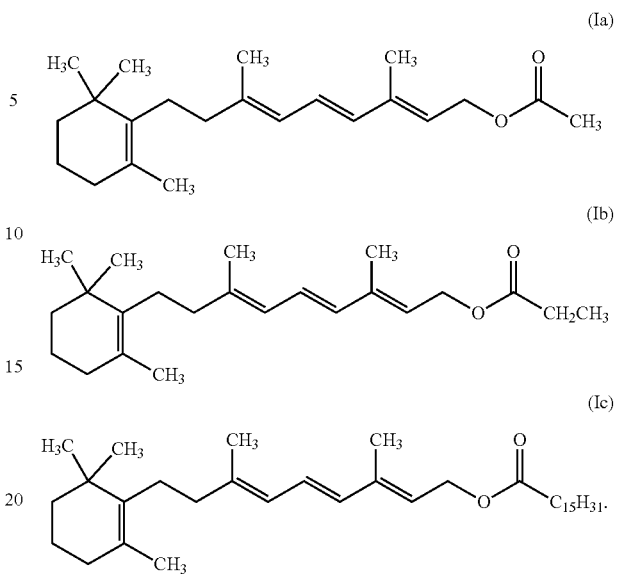

Therefore, the present invention is also relating to the compound of formula (Ia)

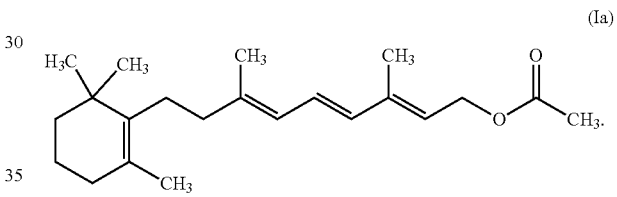

Therefore, the present invention is also relating to the compound of formula (Ib)

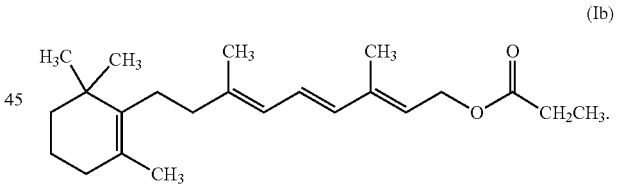

Therefore, the present invention is also relating to the compound of formula (Ic)

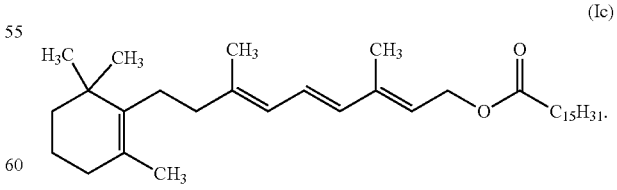

These new compounds are produced with the corresponding anhydrides according to commonly known processes starting from a compound of formula (IV) (obtained according to Law, Wing C. et al. Journal of the American Chemical Society, 1988, vol. 110, (17), p. 5915-5917).

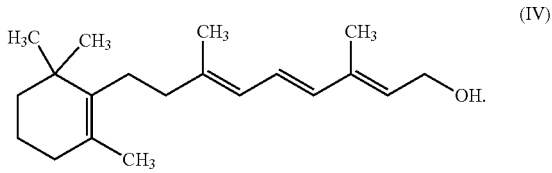 [SMILES: CC1=C(CC/C(C)=C/C=C/C(C)=C/CO)C(C)(C)CCC1]

(IV)

As stated above the process according to the present invention is one important step in the synthesis of vitamin A (and/or its derivatives).

The following examples serve to illustrate the invention. The temperature is given in ° C. and all percentages are related to the weight.

EXAMPLES

Example 1

7,8-Dihydroretinylactate (150 mg, 1.0 eq) were dissolved in toluene (5 mL) and DDQ (1.0 eq) and triethoxyamine (0.5 mol %) were added. The reaction mixture was stirred for 0.5 h at 90° C. The solution was filtered over a plug of silica and all volatiles were evaporated under reduced pressure. Purification by column chromatography afforded the desired product (54% yield).

Example 2

7,8-Dihydroretinylactate (150 mg, 1.0 eq) were dissolved in toluene (5 mL) and DDQ (1.0 eq) was added. The reaction mixture was stirred for 4 h at 90° C. The solution was filtered over a plug of silica and all volatiles were evaporated under reduced pressure. Purification by column chromatography afforded the desired product (30% yield).

Example 3

7,8-Dihydroretinal (150 mg, 1.0 eq) were dissolved in toluene (5 mL) and fluoranil (2.0 eq) was added. The reaction mixture was stirred 24 h at 60° C. The solution was filtered over a plug of silica and all volatiles were evaporated under reduced pressure. Purification by column chromatography afforded the desired product (29% yield).

Example 4

7,8-Dihydroretinyl acetate (180 mg, 1.0 eq) were dissolved in ethylacetate (20 mL) and DDQ (1.0 eq) and triethoxyamine (0.5 mol %) were added. The reaction mixture was stirred for 0.5 h at 77° C. The solution was filtered over a plug of silica and all volatiles were evaporated under reduced pressure. Purification by column chromatography afforded the desired product (74% yield).

Example 5

7,8-Dihydroretinyl acetate (181 mg, 1.0 eq) were dissolved in ethylacetate (5 mL) and DDQ (1.0 eq) and triethoxyamine (0.5 mol %) were added. The reaction mixture was stirred for 0.5 h at room temperature and 0.5 h at 77° C. The solution was filtered over a plug of silica and all volatiles were evaporated under reduced pressure. Purification by column chromatography afforded the desired product (75% yield).

The invention claimed is:

1. A process for the production of a compound of formula (II):

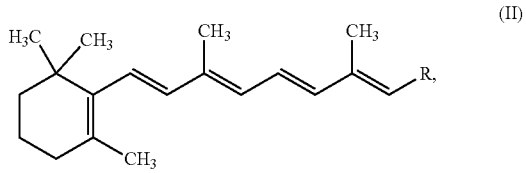

(II)

wherein
R is —CH=O or —CH$_2$OCOR', wherein R' is a —C$_1$-C$_{16}$ alkyl group,
wherein
the process comprises conducting in the presence of at least one oxidative reactant and in the presence of at least one additive compound a selective dehydrogenation of a compound of formula (I):

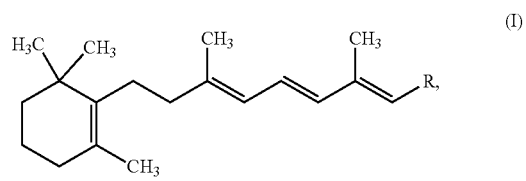

(I)

wherein
R has the same meanings as in the compound of formula (II),
wherein
the at least one oxidative reactant is a compound of formula (III):

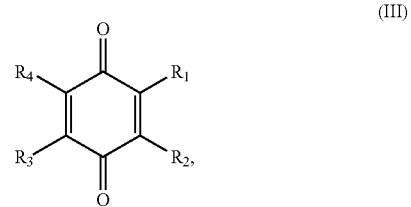

(III)

wherein
R$_1$ is —CN, —Cl or —F,
R$_2$ is —CN, —Cl or —F,
R$_3$ is —H, —CH$_3$, —Cl or —F, and
R$_4$ is —H, —CH$_3$, —Cl or —F.

2. The process according to claim 1, wherein the at least one oxidative reactant is selected from the group consisting of compounds of formulas (IIIa), (IIIb) and (IIIc):

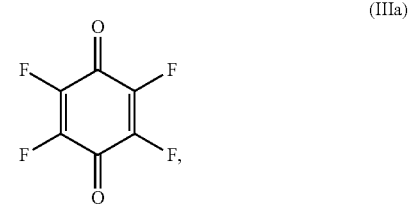

(IIIa)

-continued

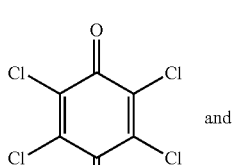
(IIIb)

and

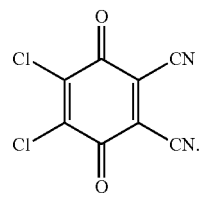
(IIIc)

3. The process according to claim 1, wherein the at least one oxidative reactant is a compound of formula (IIIc):

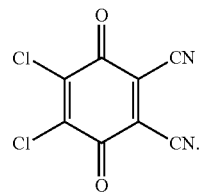
(IIIc)

4. The process according to claim 1, wherein the at least one oxidative reactant of formula (III) is present in an amount of from 0.5 mol-equivalent up to 5 mol-equivalent in relation to the compound of formula (II).

5. The process according to claim 1, wherein the at least one additive compound is selected from the group consisting of pyridine, butylhydroxyltoluol, hydroquinone and triethoxyamine.

6. The process according to claim 1, wherein the at least one additive compound is present in an amount of 0.001—1 mol-equivalent in relation to the compound of formula (II).

7. The process according to claim 1, wherein the process comprises conducting the selective dehydrogenation in the presence of at least one inert solvent.

8. The process according to claim 7, wherein the at least one inert solvent is an aromatic hydrocarbon solvent.

9. The process according to anyone of the preceding claims, wherein the process comprises conducting the selective dehydrogenation at a temperature of 0° C.—120° C.

10. The process according to claim 1, wherein R' is —$CH_3$, —$CH_2CH_3$ or —$C_{15}H_{31}$.

11. A compound of formula (Ia):

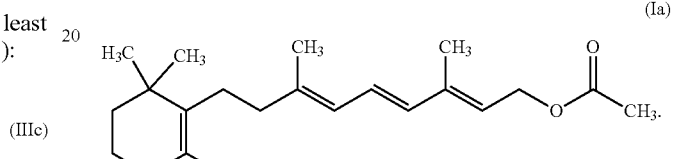
(Ia)

12. A compound of formula (Ib):

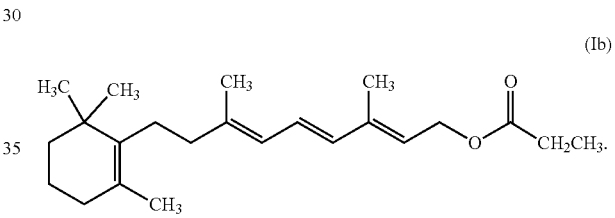
(Ib)

* * * * *